United States Patent [19]
Deom

[11] Patent Number: 5,772,438
[45] Date of Patent: Jun. 30, 1998

[54] METHOD FOR INSTALLING A PERMANENT BRIDGE BETWEEN A PAIR OF ABUTMENT TEETH

[75] Inventor: Guy Deom, Laval, Canada

[73] Assignee: Deom Design Inc., Laval, Canada

[21] Appl. No.: 813,196

[22] Filed: Mar. 7, 1997

[51] Int. Cl.$^6$ .................................................. A61C 13/12
[52] U.S. Cl. ............................................................ 433/181
[58] Field of Search ..................................... 433/180, 181

[56] References Cited

U.S. PATENT DOCUMENTS

| | | | |
|---|---|---|---|
| 1,340,089 | 5/1920 | Stone | 433/181 |
| 3,641,670 | 2/1972 | Karageorge | 433/180 |
| 4,380,435 | 4/1983 | Raeder et al. | 433/181 |
| 4,661,067 | 4/1987 | Harvey, Sr. et al. | 433/181 |
| 4,775,320 | 10/1988 | Marshall et al. | 433/180 |
| 4,950,162 | 8/1990 | Korber et al. | 433/180 |
| 5,171,147 | 12/1992 | Burgess | 433/181 |

*Primary Examiner*—John J. Wilson
*Attorney, Agent, or Firm*—Robic

[57] ABSTRACT

A method for installing a permanent bridge over a gincival crest between a pair of abutment teeth posterior to the canines, comprising a) providing a rigid infrastructure having two wings, the infrastructure being sized to extend in between and inside the abutment teeth; b) processing the abutment teeth to form retentive dental cavities large enough to receive the wings of the infrastructure; c) applying a resistant composite to the bottom of the infrastructure, curing the resistant composite that is so applied so as to fix the resistant composite to the infrastructure and thus to form a bridge, processing the bridge to remove imperfections and placing each of the wings of the infrastructure into the corresponding cavity to ensure that the so formed bridge fits over the gingival crest; d) fixing the wings of the infrastructure embedded into the formed bridge to the dental cavities of the abutment teeth by means of an adhesive; and e) filling the occlusal part of the bridge with an additional resistant composite and finishing the bridge to give the bridge the contours of a real tooth.

17 Claims, 4 Drawing Sheets

METHOD FOR INSTALLING A PERMANENT BRIDGE BETWEEN A PAIR OF ABUTMENT TEETH

BACKGROUND OF THE INVENTION a) Field of the invention

The present invention relates to a method for installing a permanent bridge between a pair of abutment teeth posterior to the canines.

b) Brief description of the prior art

In dentistry, there exists a number of well known methods for installing bridgework. These methods are efficient but characterized by high cost, destruction of existing biological material, the necessity of obtaining impressions of the affected area, and treatment that requires several extended visits to the dentist. Therefore, there is a need for a method of installing a dental bridge that overcomes the problems of the existing methods of installing bridgework.

SUMMARY OF THE INVENTION

The object of the present invention is to provide a method by which a dental bridge may be installed in a manner that:

is very economical as compared to the conventional methods;

requires only one visit to the dentist;

does not require impression and lab processing; and does not require destruction of any existing biological material, thereby avoiding posts and/or root canal treatments and/or wall cutting.

In accordance with the invention, this object is achieved with a method for installing a permanent bridge over a gincival crest between a pair of abutment teeth posterior to the canines, which comprises the steps of:

a) providing a rigid infrastructure having a central portion and two opposite flat wings, said infrastructure being in the form of an elongated gondola-shaped bar sized to extend in between and inside the abutment teeth;

b) processing the abutment teeth to form dental cavities large enough to receive and retain the wings of the infrastructure;

c) applying a layer of a primer adhesive to the infrastructure, applying a resistant composite to the central portion of the infrastructure, curing the resistant composite that is so applied so as to fix said resistant composite to the infrastructure and thus to form a bridge, processing said bridge to remove imperfections, and placing each of said flat wings of the infrastructure into the corresponding cavity to ensure that the so formed bridge fits over the gingival crest;

c') removing the bridge, inserting dental floss through the sides of the cavity and reinserting the bridge to make it sure that said dental floss may pass between the bridge and the abutment teeth once the installation is completed;

d) fixing the wings of the infrastructure embedded into the formed bridge to the dental cavities of the abutment teeth by means of a dual cure composite; and e) filling the occlusal portion of the bridge with an additional resistant composite and finishing the bridge to give said bridge the contours of a real tooth.

The method according to the invention is particularly well adapted for use when the abutment teeth (molars or prepolars) have fillings present, which face towards the infrastructure of the bridge to be installed.

In such a case, the method according to the invention comprises the basic steps of:

(a) providing a rigid infrastructure having a central portion and opposite flat wings, said infrastructure being in the form of an elongated gondola-shaped bar made of a strong bicompatible metal alloy, said bar having a width equal to at least 2 mm, a central thickness equal to at least 2 mm and a length sufficient to extend in between and over part of the abutment teeth;

(b) removing the fillings from the abutment teeth and processing said abutment teeth to form therein a pair of opposite [to leave] slightly retentive dental cavities sized to receive and retain the opposite wings of the infrastructure;

(c) applying a resistant composite under the central portion of the infrastructure from successive angles until a bridge fitting over the gingival crest is formed, inspecting the bridge that is so formed to remove imperfections and make it sure that it actually fits over the gingival crest, and placing each of the flat wings of the infrastructure that project out from the composite into the corresponding retentive dental cavities;

(d) fixing the wings of the infrastructure to the retentive dental cavities by means of a dual cure composite; and (e) applying an additional resistant composite to the occlusal portion of the bridge and finishing said bridge until it resembles a tooth.

The method according to the invention makes use of an infrastructure whose size and shape depend on the position and shape of the abutment teeth. This infrastructure can be selected among three types of infrastructures that can be sold as a kit, depending on which tooth is to be replaced (molar or premolar).

BRIEF DESCRIPTION OF THE DRAWINGS

The invention will be better understood upon reading the following detailed and non-restrictive description of it, made with reference to the accompanying drawings in which.

DETAILED DESCRIPTION OF THE INVENTION

As briefly disclosed hereinabove, the method according to the invention comprises five basic steps. Each of these steps will now be described in greater detail.

Step (a): providing a rigid infrastructure

The first step of the method according to the invention consists of providing a rigid infrastructure 1 which has 2 central portion two opposite flat wings 3, 5 and is long enough to extend in between and inside the coronal part of the abutment teeth T,T' between which the permanent bridge must be installed.

As aforesaid, the bridge is intended to be used in replacement situation posterior to canines. Thus, it is intended to be installed between premolars or molars provided that such teeth have fillings that face towards the infrastructure to be installed. Indeed, the method according to the invention is not desirable when one or both abutment teeth is or are intact. In such a case, the primary choice should preferably be a butterfly or Maryland bridge or, if money and receptive bone is no object, an implant. The adjacent teeth should also not be of different extreme levels due to a malocclusion.

The infrastructure 1 is in the form of an elongated gondola-shaped bar made of a strong biocompatible metallic alloy (BIOSIL F, INTERNATIONAL STANDARD ISO 6871). Its actual shape and size depend on position where it is intended to be installed.

Figure 1:
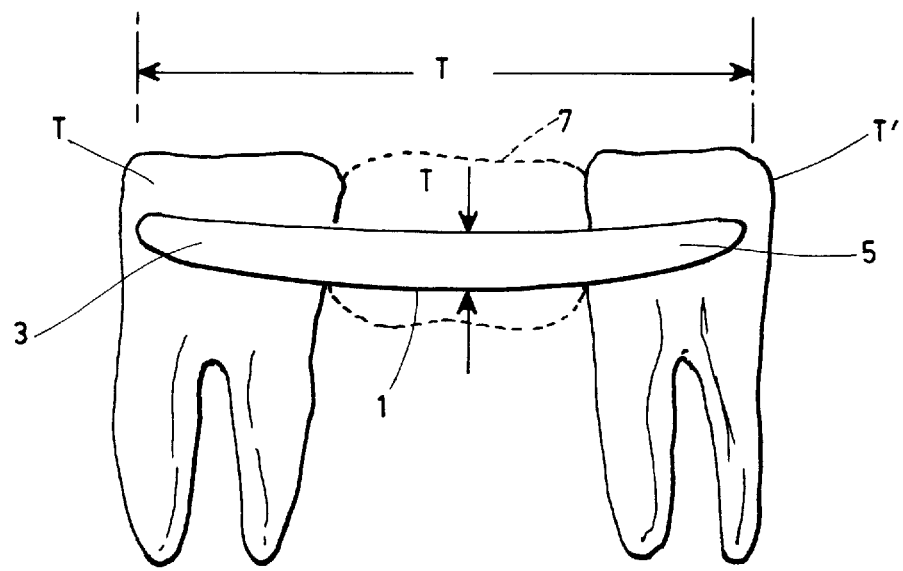
FIG. 1 is a lateral view in transcoronal transparency of a molar infrastructure of the universal type for use in the method according to the invention, the illustrated infrastructure being shown in installed position.
Figure 2:
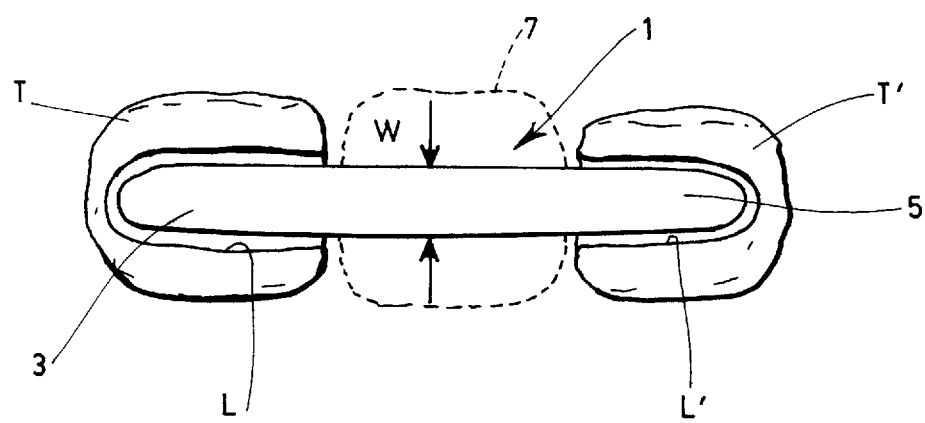
FIG. 2 is an overhead "occlusal" transcoronal view of the molar infrastructure shown in FIG. 1.
Figure 3:
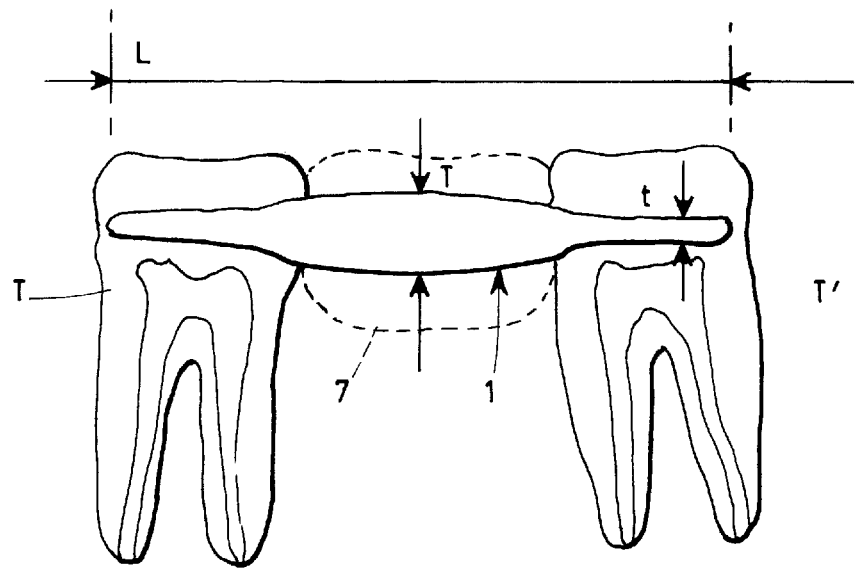
FIG. 3 is a lateral view in transcoronal transparency of a molar infrastructure of precontoured type, shown in installed position.
Figure 4:
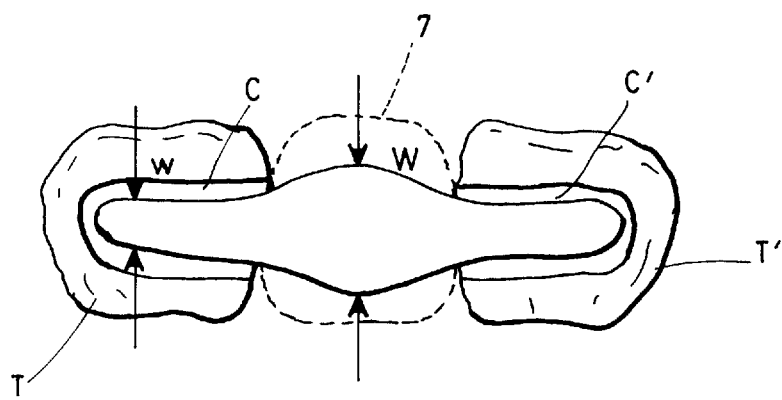
FIG. 4 is an overhead "occlusal" transcoronal view of the molar infrastructure shown in FIG. 3.
Figure 5:
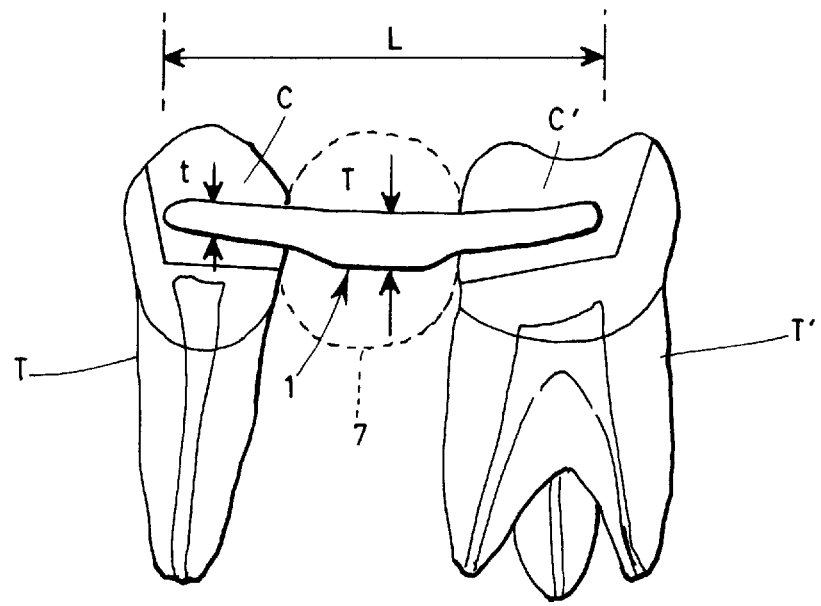
FIG. 5 is a lateral view in transcoronal transparency of a premolar infrastructure, shown in installed position.
Figure 6:
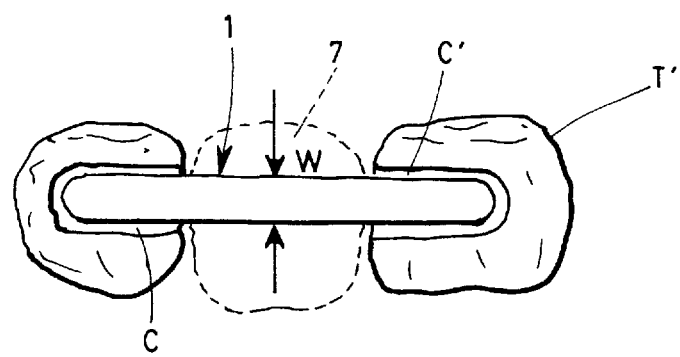
FIG. 6 is an overhead "occlusal" transcoronal view of the premolar infrastructure, shown in FIG. 5.

In most situations involving molar teeth, use can be made of a molar infrastructure 1 of the "universal" type, as shown in FIGS. 1 and 2. This universal molar infrastructure preferably has the following dimensions:
length L=about 23 mm
central thickness T=about 2 mm
wing thickness t=about 1 mm
width W=about 3 mm In some very specific situations involving molar teeth, use can be made of a molar infrastructure 1 of precontoured shape, as shown in FIGS. 3 and 4. This precontoured molar infrastructure preferably has the following dimensions:
length L=about 23 mm
central thickness T=about 3 mm
wing thickness t=about 1.5 mm
cental width W=about 6 mm
wing width w=about 3 mm In situations involving premolar infrastructure teeth, use can be made of a premolar infrastructure 1 as shown in FIGS. 5 and 6. This premolar infrastructure preferably has the following dimensions:
length L=about 19 mm
central thickness T=about 2.75 mm
wing thickness t=about 1.25
width W=about 2 mm In some other situations, it is also possible to use such a bridge to replace first premolars in quadrants using a premolar infrastructure. One of the essential conditions for this option is to have a significant filling on the distal of the canine which is retentive, and large enough to be able to insert a premolar infrastructure. For this option, the second premolar should also have a mesial-occlusal or mesial-occlusal-distal filling.

Of course, in use, one must choose amongst the three types of infrastructure disclosed hereinabove, the one that is the best adapted for the particular bridge to be installed. Such a choice can be made after the abutment teeth T,T' have been processed as will be described hereinafter (see step (b)), and thus are provided with dental cavities C,C' adapted to receive the wings 3,5 of the infrastructure 1.

If the wings 3,5 of the selected infrastructure 1 are too long and/or too large and do not move down to the bottom of the dental cavities C,C', the size of these wings can be modified with a balloon-shaped bur (not 30 shown), until they may properly be seated. In use, if is preferable to leave 1.5 to 2 mm free at the occlusal in order to maximize aesthetics by hiding the infrastructure. It is also preferable to etch the modified infrastructure 1 with a sand-jet apparatus like the one sold under the trademark MICRO-ETCHER."

Step (b): processing the abutment teeth to form dental cavities

The second step of the method according to the invention consists of removing the composite or amalgam fillings from the abutment teeth T,T' and then processing the teeth in order to form therein dental cavities C,C' of a sufficient size to accommodate the wings of the infrastructure chosen in step (a). The tooth processing may include cutting portions of the occlusal parts of the teeth, but one must always remember that it is preferable to modify the infrastructure in specific situations rather than being aggressive by cutting unnecessarily intact tooth structure.

Figure 8:
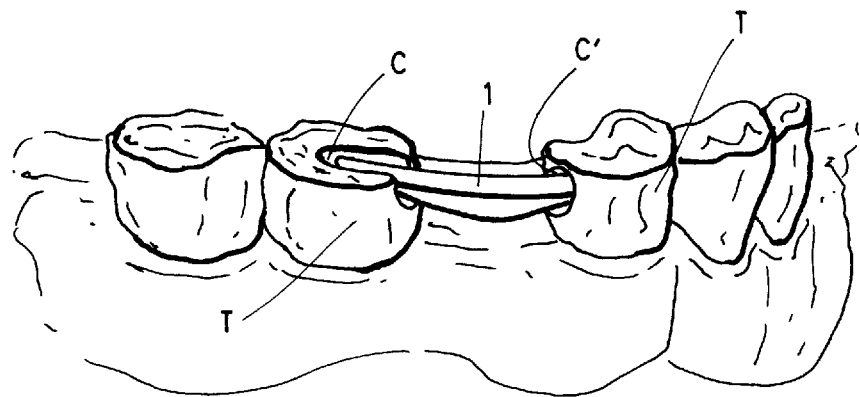
FIG. 8 is a lateral view of a infrastructure having one wing installed in a dental cavity made in the occlusal part of an adjacent tooth and another wing installed in a dental cavity in the form of an opening made in one side of the other adjacent tooth.

In situations where only one of the abutment teeth has a filling, the other abutment tooth should be processed in order to form therein the requested cavity in which the corresponding wing of the infrastructure may rest. In some particular situations like the one shown in FIG. 8, one may create an opening C" in the side of the tooth facing the gincival crest in order to receive one of wings of the infrastructure 1. Of course, this opening must be large enough to allow the wing of the infrastructure to be inserted therein.

Figure 7:
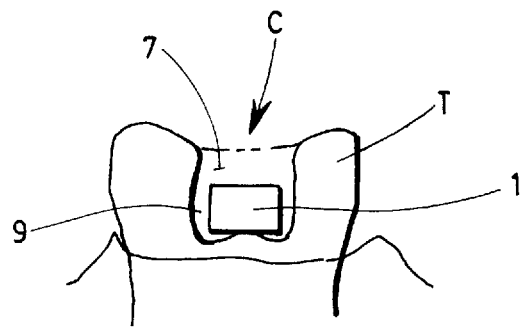
FIG. 7 is a lateral view of a premolar infrastructure, having one wing inserted into an opening made in an adjacent premolar.

In all cases, in order to ensure that the bridge does not become loose and/or fall out, the dental cavities C,C' should be made slightly retentive, as is shown in FIG. 7.

Step (c): applying composite to the pontic

The third step of the method according to the invention consists of applying a resistant composite 7 to the infrastructure 1, curing this resistant composite that is so applied so as to fix the composite to the infrastructure and thus to form a bridge, processing the bridge to remove imperfections and placing each of the wings 35 of the infrastructure 1 into the corresponding cavities C,C' to ensure that the so formed bridge fits over the gincival crest.

Figure 9:
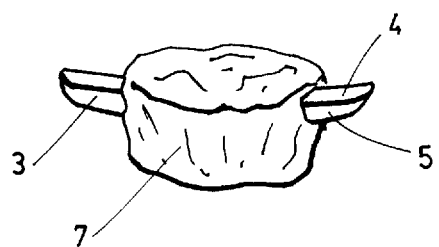
FIG. 9 is a perspective view of a bridge prepared in according with the invention, just before it is fixed to the adjacent teeth.

This step actually corresponds to the preparation of the underneath part of the bridge. The rough bridge that is so obtained is illustrated in FIG. 9.

The resistant composite that can be used in this step is known and commonly available. By way of example, reference can be made to the highly resistant composites sold under the trademarks Z100, HERCULITE, SPECTRUM or GLACIER.

Preferably, prior to the application of the resistant composite to the infrastructure, a layer of primer-adhesive can be applied with a brush to the same and cured according to the manufacturer's specifications.

Preferably also, prior to the application of the resistant composite to the pontic, an opaquer can be applied to the occlusal surface of the infrastructure to hide the metallic aspect of the infrastructure and enhance the aesthetic appearance of the bridge. To verify that any excess of so applied opaquer has not altered the fit of the infrastructure and does not hinder insertion of the infrastructure into the bottoms of the dental cavities, the infrastructure can be reinserted into the dental cavities.

In practice, a first amount of resistant composite can be applied to the first gingival portion of the infrastructure while the same is hand-held. Care must be taken not to apply composite to the portions of the infrastructure that will be close to the abutment teeth T,T'.

The infrastructure to which the composite has been so applied forms a pontic that can be positioned again with the dental cavities C,C' and pressed therein with a pair of tweezers to make it sure that the bridge fits.

In such a position, an additional amount of resistant composite can be applied to the buccal and lingual sides of the infrastructure. The same can be removed again and a further quantities of composite can be applied to its underside to make it sure that there is a slight excess of composite on the buccal and lingual sides.

After further reinsertion and removal of the pontic, the gingivomesial and gingivodistal angles under the pontic can be filled in with the same resistant composite, thereby creating the requested rough bridge (see FIG. 9).

The so created rough bridge is then positioned firmly against the bottom of the dental cavities C,C' and a wax carver can be passed over the mesial, distal and abutment tooth joint to ensure that no composite material has fallen under the retentive part of the tooth.

After it has been verified that no resistant composite remains under the retentive gingivoaxial part of the abutment teeth T,T', the composite is cured. The bridge is then removed and examined. The resistant composite that has been added to the pontic should be in the form of a saddle closely fitted to the gums and close to the gingival ridge. Of course, any visible imperfections (bumps, bubbles, . . . ) should be corrected.

Preferably, the bridge that has been so prepared should be reinserted in the dental cavities C,C' and an attempt should be made to pass dental floss through the sides of the gum cavity near the abutment teeth. If there is difficulty in passing dental floss through, the underneath portion of the near the abutment teeth should be polished until dental floss can easily be passed through, thereby allowing for proper oral hygiene techniques to be employed.

It is worth mentioning that, normally, it is up to a dental technician to fabricate the requested bridge from impressions taken by a dentist. In accordance with the invention, it is the dentist who manufactures the bridge, and more especially the part of the bridge that is underneath the pontic.

Step (d): fixing the bridge

The fourth step of the method according to the invention consists of fixing the bridge prepared in step (e) in the dental cavities C,C'.

Preferably, prior to inserting the wings 3,5 projecting from the bridges into the dental cavities C,C', said cavities can be prepared so as to be as secure as possible, by acid-etching treatment and application of a glass ionomer liner/base. Similarly, tissues which come into contact with the bottom of the bridge may be treated to remain healthy. In practice, the dental cavities C,C' should be prepared as securely as the situation warrants with care taken to avoid contamination. If the cavity preparation is a medial-occlusal-distal, a clear plastic matrix should be used, as usual, rehabilitation of cavities in such situations.

Then, a fine layer of a known adhesive 9 (see FIG. 7) like the dual-cure composite sold under the trademark VARIO-LINK or any other dual cure composite, should be applied and cured beneath the wings of the bridge.

As aforesaid, the dual-cure composite 9 used as an adhesive can be mixed and spread over the bottom of the dental cavities C,C'. Then, each wing 3,5 of the bridge is inserted into the dental cavities C,C' and adjusted rapidly so as to be seated properly. The seating of the bridge is accomplished by means of the automatic hold of the dual-cure composite. Excess dual-cure composite at the external-gingival angles that flows out when the is "pushed" into the bottom of the dental cavities, should be removed by means of a wax carver or round periodontal probe. Hardening of the dual-cure composite may be accelerated by curing from the occlusal surface.

Step (e): finishing the occlusal portion of tooth

The fifth and last step of the method according to the invention consists of finishing the occlusal portion of the tooth.

To do so, an additional amount of resistant composite 7 can be added to the top of the wings 3,5 of the bridge in the dental cavities of the abutment teeth T,T' (see FIG. 7). The occlusal of the teeth can then be sculptured and fine finished.

Finally, the occlusal part of the pontic can also be filled in with the same resistant composite, sculptured and fine finished.

When sculpturing and fine finishing the occlusal portion, the following precautions should be taken relative to occlusion and morphology. Canine guidance should be enhanced and balancing contacts avoided on the pontics lingual or palatal cuspid; the cuspids of the teeth should be sculptured rounder than is customary; and the should not be made to large in the buccallingual region.

A number of advantages accrue from the method according to the invention.

First of all, the biological cost is minimal since the pulp and nerve tissue are conserved, dentin within the root canal is preserved, the buccal and lingual enamel are preserved and no wall cutting is required.

Secondly, the method according to the invention is very economical as compared to the methods associated with traditional bridges and implants which require several visits to the dentist's office and dental impressions that give rise to associated laboratory costs.

Thirdly, the method according to the invention is faster than the traditional methods of installing bridgework because the bridge can be installed during one visit, thereby reducing the chairside time for the patient. Additionally, the root canal treatment associated with many methods of installing bridgework is unnecessary.

Fourthly, the precision of adaptation afforded by this method is very good.

Fifthly, the bridge that is created is easy to repair. Chips, dents, and other damage may be repaired by reapplying composite to the affected area.

While the present invention has been described in great detail, it will be understood that obvious modifications may become apparent to those of ordinary skill in the art.

I claim:

1. A method for installing a permanent bridge over a gingival crest between a pair of abutment teeth posterior to the canines, said method comprising:

a) providing a rigid infrastructure having a central portion and two opposite flat wings, said infrastructure being in the form of an elongated gondola-shaped bar sized to extend in between and inside the abutment teeth;

b) processing the abutment teeth to form dental cavities large enough to receive and retain the wings of the infrastructure;

c) applying a layer of a primer adhesive to the infrastructure, applying a resistant composite to the central portion of the infrastructure, curing the resistant composite that is so applied so as to fix said resistant composite to the infrastructure and thus to form a bridge, processing said bridge to remove imperfections, and placing each of said flat wings of the infrastructure into the corresponding cavity to ensure that the so formed bridge fits over the gingival crest;

c') removing the bridge, inserting dental floss through the sides of the cavity and reinserting the bridge to make it sure that said dental floss may pass between the bridge and the abutment teeth once the installation is completed;

d) fixing the wings of the infrastructure embedded into the formed bridge to the dental cavities of the abutment teeth by means of a dual cure composite; and e) filling the occlusal portion of the bridge with an additional resistant composite and finishing the bridge to give said bridge the contours of a real tooth.

2. The method of claim 1 wherein the infrastructure provided in step a) is a universal molar infrastructure.

3. The method of claim 1 wherein the infrastructure provided in step a) is a precontoured molar infrastructure.

4. The method of claim 1 wherein the infrastructure provided in step a) is a premolar infrastructure.

5. A method for installing a permanent bridge in a gingival crest between a pair of abutment teeth that are posterior to the canines and have fillings therein, said method comprising:

(a) providing a rigid infrastructure having a central portion and opposite flat wings, said infrastructure being in the form of an elongated gondola-shaped bar made of a strong bicompatible metal alloy, said bar having a width equal to at least 2 mm, a central thickness equal to at least 2 mm and a length sufficient to extend in between and over part of the abutment teeth;

(b) removing the fillings from the abutment teeth and processing said abutment teeth to form therein a pair of opposite slightly retentive dental cavities sized to receive and retain the opposite wings of the infrastructures;

(c) applying a resistant composite under the central portion of the infrastructure from successive angles until a bridge fitting over the gingival crest is formed, inspecting the bridge that is so formed to remove imperfections and make it sure that it actually fits over the gingival crest, and placing each of the flat wings of the infrastructure that project out from the composite into the corresponding retentive dental cavities;

(d) fixing the wings of the infrastructure to the retentive dental cavities by means of a dual cure composite; and (e) applying an additional resistant composite to the occlusal portion of the bridge and finishing said bridge until it resembles a tooth.

6. The method of claim 5 wherein step a) also comprises modifying the wings of the infrastructure with a balloon-shaped bur.

7. The method of claim 5 wherein prior to carrying out step c), a layer of primer adhesive is applied to the infrastructure.

8. The method of claim 5 wherein prior to carrying out step c), a layer of opaquer is applied to the occlusal surface of the infrastructure to maximize aesthetics.

9. The method of claim 5 wherein prior to carrying out step d), the bridge is removed, dental floss is inserted through the sides of the gum cavity and the bridge is reinserted to make sure that dental floss may pass in between the bridge and the abutment teeth once the installation is complete.

10. The method of claim 5 wherein prior to carrying out step d), a fine layer of adhesive is cured on the side of the bridge that comes into contact with the gincival crest.

11. The method of claim 5, wherein:

prior to carrying out step c), a layer of primer adhesive is applied to the infrastructure and a layer of opaque is applied to the occlusal surface of the infrastructure to maximize aesthetics; and prior to carrying out step d), the bridge is removed, dental floss is inserted through the sides of the gum cavity and the bridge is reinserted to make it sure that said dental floss may pass in between the bridge and the abutment teeth once the installation is complete.

12. The method of claim 11 wherein the infrastructure provided in step a) is a universal molar infrastructure.

13. The method of claim 11 wherein the infrastructure provided in step a) is a precontoured molar infrastructure.

14. The method of claim 11 wherein the infrastructure provided in step a) is a premolar infrastructure.

15. The method of claim 5 wherein the infrastructure provided in step a) is a universal infrastructure.

16. The method of claim 5 wherein the infrastructure provided in step a) is a precontoured molar infrastructure.

17. The method of claim 5 wherein the infrastructure provided in step a) is a premolar infrastructure.

* * * * *